(12) United States Patent
Takai

(10) Patent No.: US 9,326,679 B2
(45) Date of Patent: May 3, 2016

(54) MEDICAL SYSTEM

(75) Inventor: Motoya Takai, Matsudo (JP)

(73) Assignee: Canon Kabushiki Kaisha, Tokyo (JP)

( * ) Notice: Subject to any disclaimer, the term of this patent is extended or adjusted under 35 U.S.C. 154(b) by 159 days.

(21) Appl. No.: 14/008,507

(22) PCT Filed: Mar. 19, 2012

(86) PCT No.: PCT/JP2012/001881
§ 371 (c)(1),
(2), (4) Date: Sep. 27, 2013

(87) PCT Pub. No.: WO2012/132301
PCT Pub. Date: Oct. 4, 2012

(65) Prior Publication Data
US 2014/0028975 A1    Jan. 30, 2014

(30) Foreign Application Priority Data

Mar. 31, 2011    (JP) .................................. 2011-079363

(51) Int. Cl.
*A61B 3/14* (2006.01)
*A61B 3/10* (2006.01)

(52) U.S. Cl.
CPC ...................................... *A61B 3/102* (2013.01)

(58) Field of Classification Search
USPC ......... 351/206, 205, 200, 209, 210, 211, 221, 351/222, 243, 245, 246
See application file for complete search history.

(56) References Cited

U.S. PATENT DOCUMENTS

| 2007/0252951 A1 | 11/2007 | Hammer et al. |
| 2009/0268020 A1 | 10/2009 | Buckland et al. |
| 2010/0321700 A1 | 12/2010 | Hirose et al. |
| 2013/0093995 A1* | 4/2013 | Suehira et al. ................ 351/206 |

FOREIGN PATENT DOCUMENTS

| CN | 101674770 A | 3/2010 |
| CN | 101791213 A | 8/2010 |
| EP | 2130486 A1 | 12/2009 |
| JP | H01023134 A | 1/1989 |
| JP | 2009291252 A | 12/2009 |
| JP | 2010181172 A | 8/2010 |
| WO | 2010/089833 A1 | 8/2010 |

* cited by examiner

*Primary Examiner* — Scott J Sugarman
*Assistant Examiner* — Brandi Thomas
(74) *Attorney, Agent, or Firm* — Canon USA Inc. IP Division

(57) ABSTRACT

A medical system includes an acquisition unit configured to acquire a tomographic image of an object to be examined based on a combined beam generated by combining a return beam returning from the object to be examined illuminated with a measuring beam and a reference beam corresponding to the measuring beam, a focus position changing unit configured to change a focus position on the object to be examined; an optical-path-length difference changing unit configured to change a difference in optical path lengths between the measuring beam and the reference beam, and a control unit configured to control the optical-path-length difference changing unit so that the difference in the optical path length is within a predetermined range and then receive an instruction to the focus position changing unit to make a change.

7 Claims, 3 Drawing Sheets

MEDICAL SYSTEM

TECHNICAL FIELD

The present invention relates to a medical system used in ophthalmologic examination and treatment, for example.

BACKGROUND ART

Among the ophthalmic apparatuses, the major ones are those which use optical coherence tomography (OCT) to acquire tomographic images of a fundus of a subject's eye at high resolution, and scanning laser ophthalmoscopes (SLO).

Japanese Patent Application Laid-Open No. 2009-291252 discusses a technique in which an examiner performs alignment with respect to a subject's eye using a joystick while observing an observation image of an anterior eye portion of the subject's eye on a monitor, and, after completion of the alignment, obtains an SLO fundus image. At this time, by pressing an auto-focusing start switch, the examiner can move a focus lens disposed in an SLO optical system based on the SLO fundus image. After the focus lens disposed in the SLO optical system is moved, a focus lens disposed in an OCT optical system is moved based on the SLO fundus image to perform rough auto-focusing in the OCT optical system. A reference mirror is then moved based on an OCT tomographic image to automatically adjust a coherence gate and to perform precise auto-focusing in the OCT optical system.

Japanese Patent Application Laid-Open No. 2010-181172 also discusses a technique in which an examiner moves a fundus camera unit toward a subject by operating a control lever, and switches an image on a display screen from an image of an anterior eye portion of the subject's eye to an observation image of a fundus thereof to adjust alignment. In this technique, after the image is switched, the examiner turns on an alignment light source to project alignment bright points onto the subject's eye. After the alignment adjustment is complete, the examiner adjusts focusing. Then, upon a determination that a proper alignment state has been achieved, luminance values of an OCT tomographic image obtained by moving a reference mirror are analyzed to automatically detect the OCT tomographic image. In Japanese Patent Application Laid-Open No. 2010-181172, the alignment adjustment may be performed manually or automatically.

CITATION LIST

Patent Literature

PTL 1: Japanese Patent Application Laid-Open No. 2009-291252

PTL 2: Japanese Patent Application Laid-Open No. 2010-181172

PTL 3: Japanese Patent Application Laid-Open No. 01-23134

SUMMARY OF INVENTION

Technical Problem

In these techniques, it is desirable that an ophthalmic apparatus is configured to enable an examiner to select whether to adjust alignment, a focus position, and a coherence gate position manually or automatically. In that case, the alignment, the focus position, and the coherence gate position are preferably adjusted automatically in this order. This is because these adjustments are made using respective images of an anterior eye portion, a fundus, and a target part of the fundus, and are therefore preferably performed in sequence starting from the adjustment for the largest area. During adjustment of the coherence gate position, if the examiner manually adjusts the alignment and/or the focus position, a suitable coherence gate position cannot be determined indefinitely, causing an unnecessary increase in the time required for the adjustment

Solution to Problem

According to an aspect of the present invention, a medical system includes an acquisition unit configured to acquire a tomographic image of an object to be examined based on a combined beam generated by combining a return beam returning from the object to be examined illuminated with a measuring beam and a reference beam corresponding to the measuring beam, a focus position changing unit configured to change a focus position on the object to be examined;

an optical-path-length difference changing unit configured to change a difference in optical path lengths between the measuring beam and the reference beam, and a control unit configured to control the optical-path-length difference changing unit so that the difference in the optical path length is within a predetermined range and then receive an instruction to the focus position changing unit to make a change.

Advantageous Effects of Invention

According to an aspect of the present invention, after completion of automatic adjustment of a coherence gate position, an examiner can manually adjust a focus position. During the automatic adjustment of the coherence gate position, the examiner cannot manually adjust the focus position. This configuration can prevent an unnecessary increase in the time required for the adjustment.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Figure 1A:
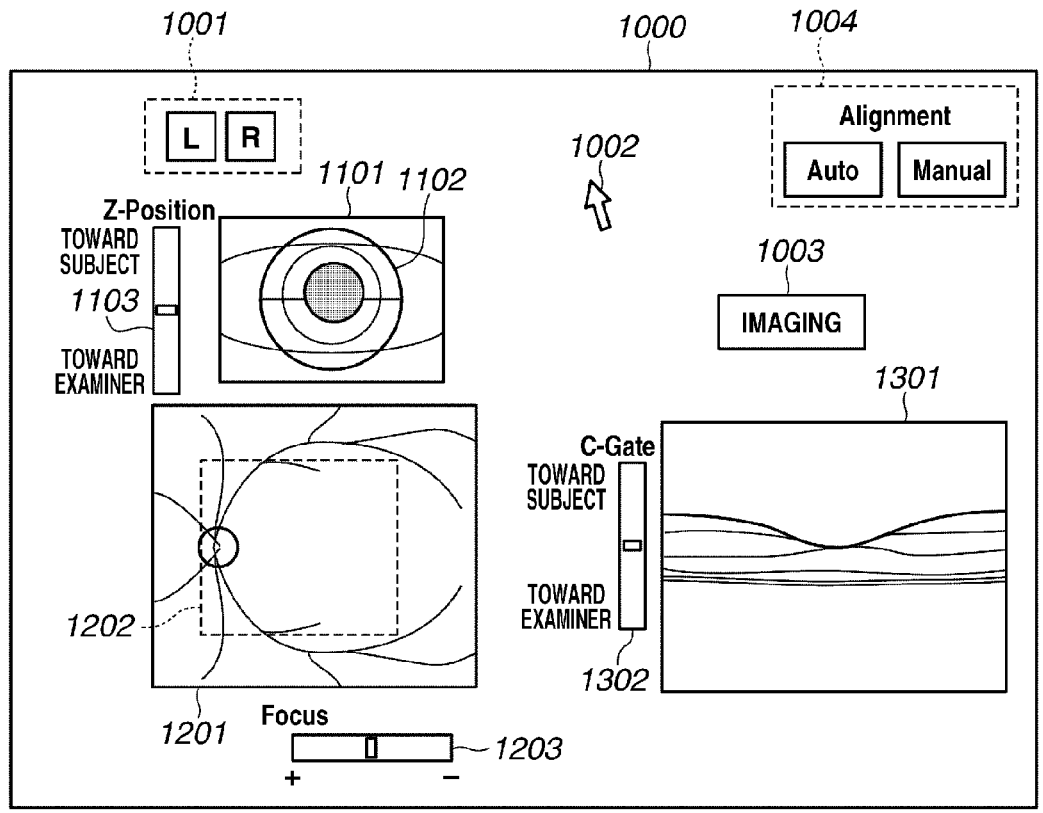
FIG. 1A illustrates a measurement screen of an ophthalmic system according to an exemplary embodiment of the present invention.

Various exemplary embodiments, features, and aspects of the invention will be described in detail below with reference to the drawings.

With an ophthalmic system (or an ophthalmic apparatus) according to an exemplary embodiment, after completion of automatic adjustment (also referred to as an automatic change) of a coherence gate position, an examiner can perform manual adjustment (also referred to as a manual change) of a focus position. During the automatic adjustment (during the automatic change) of the coherence gate position (in other words, during the time period in which an optical-path-length difference changing unit exercises control), the examiner cannot manually adjust the focus position (that is, cannot give an instruction to change the focus position).

More specifically, manual adjustment is prohibited during automatic adjustment. When the automatic adjustment is completed, the manual adjustment is permitted (the prohibition is removed). This configuration can prevent an unnecessary increase in the time required for the adjustment. A change in the focus position is also referred to as a focus position changing unit. A change in the coherence gate position is also referred to as an optical-path-length difference changing unit. The present invention can be applied not only to an ophthalmic systems, but also to a medical system (or a medical apparatus), such as an endoscope, used to observe the human skin and other objects to be examined.

The term "coherence gate" as used herein means a position in an optical path of a measuring beam corresponding to an optical path of a reference beam. The position of the coherence gate can be changed by varying a difference in optical path length between the measuring beam and the reference beam using an optical-path-length difference changing unit. The optical-path-length difference changing unit may be configured to move the position of a reference mirror along the optical axis, or may be configured to move the apparatus along the optical axis with respect to the subject's eye. Examples of the optical-path-length difference changing unit may include a movable stage provided for the reference mirror and the apparatus.

The ophthalmic system or the ophthalmic apparatus according to the present exemplary embodiment may be configured in such a manner that an examiner can select either an automatic mode or a manual mode. In the automatic mode, alignment, a focus position, and a coherence gate position are automatically adjusted in this order (instead of the focus position, polarization of at least either a measuring or reference beam, or the light quantity of the reference beam may be adjusted by a light changing unit). In the manual mode, these are adjusted manually. For example, alignment mode selection buttons 1004 are provided on a measurement screen 1000. If the examiner selects the automatic mode ("Auto"), then the manual mode ("Manual") (a mode in which the examiner can give instructions to make a change by an instruction unit) will be automatically selected after completion of the automatic adjustment. Such a configuration enables the examiner to manually make fine adjustment after automatic coarse adjustment, so that the efficiency of the adjustment can be increased.

General Configuration of Apparatus

Figure 2A:
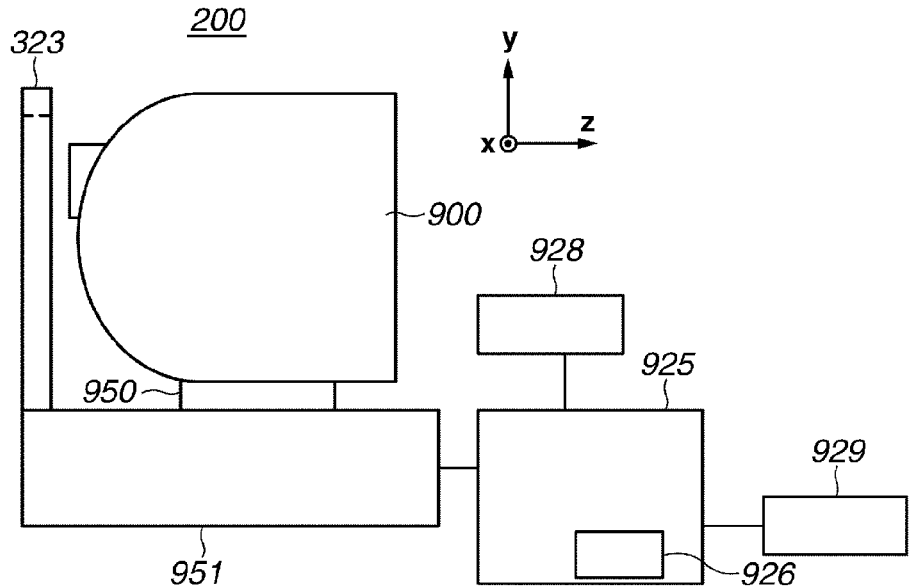
FIG. 2A illustrates components in an ophthalmic apparatus according to the exemplary embodiment.

The general configuration of an ophthalmic apparatus according to the present exemplary embodiment will be described with reference to FIG. 2A, which is a side view thereof. An optical head 900 is a measuring optical system for obtaining an image of an anterior eye portion, and a two-dimensional image and a tomographic image of a fundus of the eye. With a stage unit 950 (also referred to as a moving unit), the optical head 900 is movable with respect to a base unit 951. The stage unit 950 is moved by a motor or the like in X-, Y-, and Z-directions in FIG. 2A. The base unit 951 includes a spectroscope which will be described below.

A personal computer 925, which serves as a control unit for the stage unit 950 as well, can construct tomographic images, while controlling the stage unit 950. A hard disk 926, which also serves as a storage unit for storing information about a subject, stores a program for capturing tomographic images, for example. A display control unit (not illustrated) causes a display unit 928, such as a monitor, to display acquired images and other images. An input unit 929 provides an instruction to the personal computer 925. More specifically, the input unit 929 includes a keyboard and a mouse (also referred to as a pointing device). A chinrest 323 is provided to fix a chin and a forehead of a subject.

Configurations of Measuring Optical System and Spectroscope

Figure 2B:
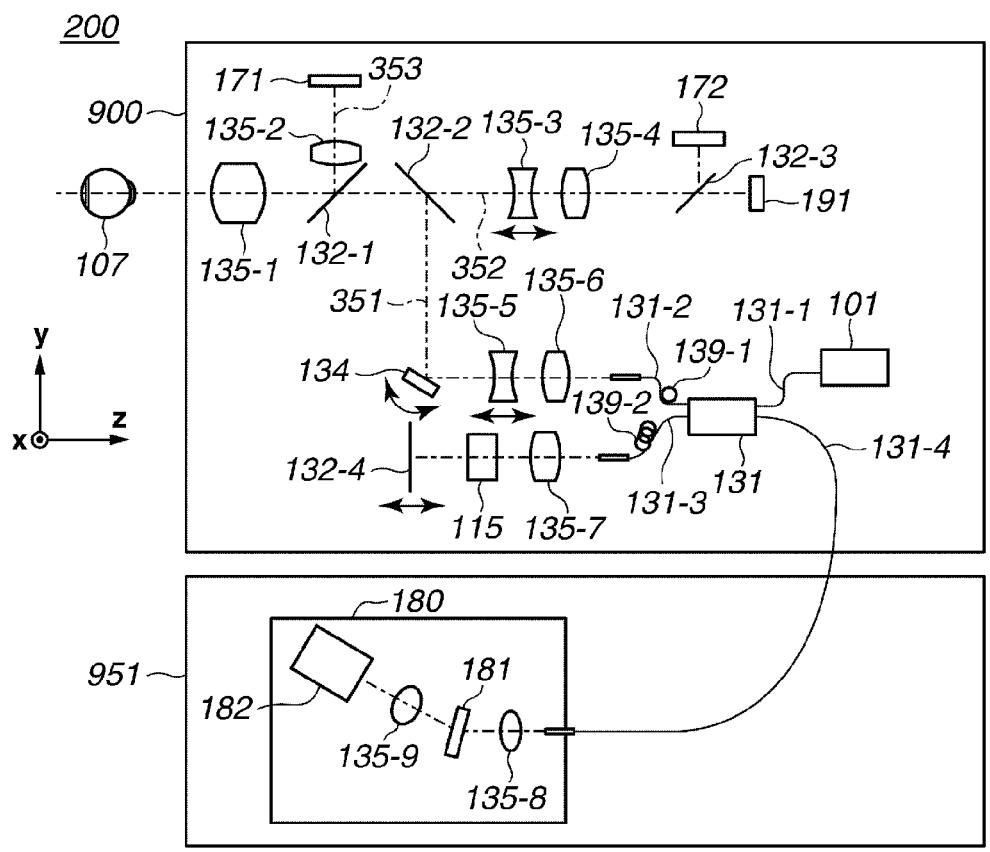
FIG. 2B illustrates components in an ophthalmic apparatus according to the exemplary embodiment.

The configurations of the measuring optical system and a spectroscope in the ophthalmic apparatus according to the present exemplary embodiment will be described below with reference to FIG. 2B.

The internal configuration of the optical head 900 will be first described. An objective lens 135-1 is placed to face a subject's eye 107. On an optical axis of the objective lens 135-1, a first dichroic mirror 132-1 and a second dichroic mirror 132-2 split light by wavelength band into an optical path 351 of an OCT optical system, an optical path 352 for observation of the fundus and for a fixation lamp, and an optical path 353 for observation of the anterior eye portion. Likewise, a third dichroic mirror 132-3 splits the light in the optical path 352 by wavelength band into an optical path to a fundus observation charge-coupled device (CCD) 172 and an optical path to a fixation lamp 191. The optical head 900 further includes lenses 135-3 and 135-4. The lens 135-3 is driven by a motor (not illustrated) to adjust focusing for the fixation lamp and for observation of the fundus. The CCD 172 has sensitivity to the wavelength of illumination light (not illustrated) provided for observation of the fundus, specifically, a wavelength of about 780 nm. The fixation lamp 191 produces visible light to facilitate fixation of the subject's eye 107.

The optical system for observation of the fundus may include an optical system, such as a scanning laser ophthalmoscope (SLO), for example. In the optical path 353, a lens 135-2 and an anterior eye observation infrared CCD 171 are provided. The CCD 171 has sensitivity to the wavelength of illumination light (not illustrated) provided for observation of the anterior eye portion, specifically, a wavelength of about 970 nm. Further, in the optical path 353, an image splitting prism (not illustrated) is provided, enabling the distance from the optical head 900 to the subject's eye 107 in the Z-direction to be detected as split images obtained in an anterior eye observation image.

The optical path 351 forms the OCT optical system as described previously and is used to acquire tomographic images of the fundus of the subject's eye 107. More specifically, the optical path 351 is used to obtain an interference signal for forming a tomographic image. An XY scanner 134 scans the fundus with a light beam. The XY scanner 134, illustrated as a mirror, performs scanning in the two axial directions X and Y. The optical head 900 further includes lenses 135-5 and 135-6. The lens 135-5 is driven by a motor (not illustrated) to perform a focus adjustment for focusing a light beam from a light source 101 emitted from a fiber 131-2 onto the fundus of the subject's eye 107. The fiber 131-2 is connected to an optical coupler 131. Concurrently, due to the focus adjustment, light from the fundus of the subject's eye 107 forms a spot image and is incident on an edge of the fiber 131-2.

The configurations of the optical path from the light source 101, a reference optical system, and a spectroscope will be described below. The light source 101, a mirror 132-4, a dispersion compensation glass 115, the optical coupler 131, single-mode optical fibers 131-1 to 131-4, which are connected to the optical coupler 131 as an integral part thereof, a lens 135-7, and a spectroscope 180 form a Michelson interferometer. A light beam emitted from the light source 101 travels through the optical fiber 131-1 and the optical coupler 131 in which the light beam is split into a measuring beam to the optical fiber 131-2 and a reference beam to the optical fiber 131-3.

The measuring beam travels through the optical path of the above-described OCT optical system to illuminate the fundus of the subject's eye 107, which is an object to be observed. The measuring beam is reflected and scattered by the retina, and thus travels to the optical coupler 131 through the same optical path. The reference beam passes through the optical fiber 131-3, the lens 135-7, and the dispersion compensation glass 115 to reach the mirror 132-4 for reflection. The dispersion compensation glass 115 is inserted to compensate for dispersion of the measuring beam and the reference beam. The reference beam returns through the same optical path to the optical coupler 131. The optical coupler 131 combines the measuring beam and the reference beam into interference light (also referred to as combined light). When the measuring beam and the reference beam have substantially the same optical path length, interference occurs. The mirror 132-4 is held by a motor and a drive mechanism (not illustrated) so as to be adjustable in the direction of the optical axis. Thus, the optical path length of the reference beam can be adjusted to be equal to the optical path length of the measuring beam that varies depending on the subject's eye 107. The interference light is guided to the spectroscope 180 via the optical fiber 131-4.

A polarization adjusting unit 139-1 for the measuring beam is provided in the optical fiber 131-2. A polarization adjusting unit 139-2 for the reference beam is provided in the optical fiber 131-3. The polarization adjusting units 139-1 and 139-2 include some portions of the optical fibers 131-2 and 131-3 each routed in the shape of a loop. The polarization states of the measuring beam and the reference beam can be adjusted to each other by turning these loop-shaped portions with the longitudinal direction of each fiber being the center, and thereby twisting the fibers 131-2 and 131-3. In the apparatus according to the present exemplary embodiment, the polarization states of the measuring beam and the reference beam are adjusted and fixed in advance. The spectroscope 180 includes lenses 135-8 and 135-9, a diffraction grating 181, and a line sensor 182. The interference light emitted from the optical fiber 131-4 is collimated into approximately parallel light by the lens 135-8. The parallel light is then dispersed by the diffraction grating 181 to form an image on the line sensor 182 through the lens 135-3.

The light source 101 and its periphery will be described in more detail below. The light source 101 is a super luminescent diode (SLD), a typical low-coherence light source. The light source 101 has a center wavelength of 855 nm and a wavelength bandwidth of about 100 nm. The bandwidth, which affects the resolution of an acquired tomographic image in the direction of the optical axis, is an important parameter. In the present exemplary embodiment, the type of light source employed is an SLD. However, any other type of light source, for example, an amplified spontaneous emission (ASE) device, may also be used so long as low-coherence light can be emitted. Since a human eye is an object to be measured, near infrared light is suitable as the center wavelength. The center wavelength, which affects the resolution of an acquired tomographic image in the transverse direction, is preferably a short wavelength. For those two reasons, the center wavelength is set to 855 nm.

In the present exemplary embodiment, a Michelson interferometer is employed. However, a Mach-Zehnder interferometer may also be used. When a difference in the amount of light between the measuring beam and the reference beam is relatively small, a Michelson interferometer, in which a single splitting and combining unit is provided, is preferable to a Mach-Zehnder interferometer, in which a splitting unit and a combining unit are provided separately.

Method for Acquiring Tomographic Image

Next, a method for acquiring a tomographic image will be described. A control unit (not illustrated) acquires a tomographic image of a desired portion of the fundus of the subject's eye 107 by controlling the XY scanner 134. First, the measuring beam 105 is scanned in the X-direction, so that information for a predetermined number of imaging lines is captured by the line sensor 182 from an imaging area on the fundus in the X-direction. A fast Fourier transform (FFT) is performed on a luminance distribution on the line sensor 182 obtained at a position in the X-direction. The linear luminance distribution resulting from the FFT is converted into density information or color information for display on the monitor 928. This density or color information is referred to as an A-scan image. A two-dimensional image obtained by arranging a plurality of A-scan images is referred to as a B-scan image. After capturing a plurality of A-scan images for constructing a single B-scan image, the scanning position in the Y-direction is moved, and scanning is performed again in the X-direction to obtain a plurality of B-scan images. The examiner can make a diagnosis on the subject's eye 107 by looking at the plurality of B-scan images or a three-dimensional tomographic image constructed from the plurality of B-scan images, displayed on the monitor 928.

Measurement Screen

Figure 1B:
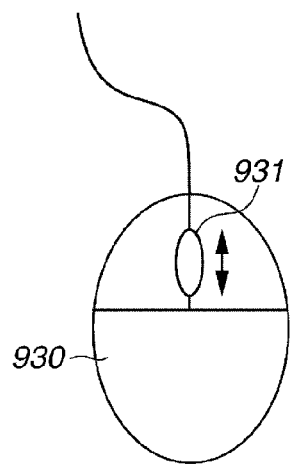
FIG. 1B illustrates a mouse with a mouse wheel.

With reference to FIGS. 1A and 1B, a measurement screen 1000, which is displayed in the display screen, will be described. An anterior eye observation screen 1101 displays an image acquired by the anterior eye observation CCD 171. A fundus two-dimensional image display screen 1201 displays an image acquired by the fundus observation CCD 172. Split images 1102 of an anterior eye portion are obtained using the image splitting prism provided in the anterior eye observation system. The split images 1102 are used in performing alignment. Japanese Patent Application Laid-Open No. 01-23134 discusses application of an image splitting prism to a fundus camera. The fundus two-dimensional image display screen 1201 includes an imaging area 1202 in which a tomographic image with respect to a fundus image is captured. The tomographic image is displayed on a tomographic image display screen 1301 in a display position based on the coherence gate position.

Buttons 1001 are used to switch the subject's eye between the right and left eyes. When the examiner presses either the L or R button, the optical head 900 is moved to the position of the left or right eye corresponding to the pressed button. As the examiner moves the mouse on a desk, for example, a position of the cursor 1002 moves correspondingly. In the ophthalmic apparatus according to the present exemplary embodiment, alignment or the like may be changed according to the position of the cursor 1002 detected by a position detecting unit (not illustrated). The position detecting unit (not illustrated) can calculate the position of the cursor 1002 from the pixel position of the cursor 1002 on the display screen. Predetermined areas are defined on the display screen. When the cursor 1002 is positioned within the pixels of those predetermined areas, the examiner can perform respective adjustments determined for those areas.

The examiner can operate the mouse by rotating a mouse wheel. As illustrated in FIG. 1B, generally a mouse wheel 931 is disposed on an upper portion of the mouse 930. By rotating the mouse wheel 931, the examiner can give an instruction to make adjustment corresponding to the image on a display area on which the cursor 1002 is positioned. For example, when the cursor 1002 is positioned on an anterior eye portion image display area, the examiner can adjust alignment. When the cursor 1002 is positioned on a fundus image display area, the examiner can adjust a focus position on the fundus. When the cursor 1002 is positioned on a tomographic image display area, the examiner can adjust a coherence gate position. In this case, the examiner has selected "Manual" of the alignment mode selection buttons 1004 on the measurement screen 1000. The examiner can also give instructions to make adjustments, such as an alignment adjustment, by operating the mouse 930 differently, for example, by dragging. After completion of adjustments, such as an alignment adjustment, the examiner presses an imaging button 1003 to capture a required image.

Sliders which are disposed in the vicinity of the respective images are used to make adjustments. A slider 1103 is used to adjust the position of the optical head 900 in the Z-direction with respect to the subject's eye 107. A slider 1203 is used to adjust the focus position. A slider 1302 is used to adjust the coherence gate position. In adjusting the focus position, the lenses 135-3 and 135-5 are moved in the directions indicated by arrows illustrated in FIG. 2B to make an adjustment for achieving focus on the fundus. In adjusting the coherence gate position, the mirror 132-4 is moved in the directions indicated by an arrow illustrated in FIG. 2B to allow observation of the tomographic image in a desired position on the tomographic image display screen 1301. These sliders 1103, 1203, and 1302 also move in conjunction with an operation of the mouse wheel 931 by the examiner when the cursor 1002 is positioned on the respective images.

Automatic Imaging

Figure 3:
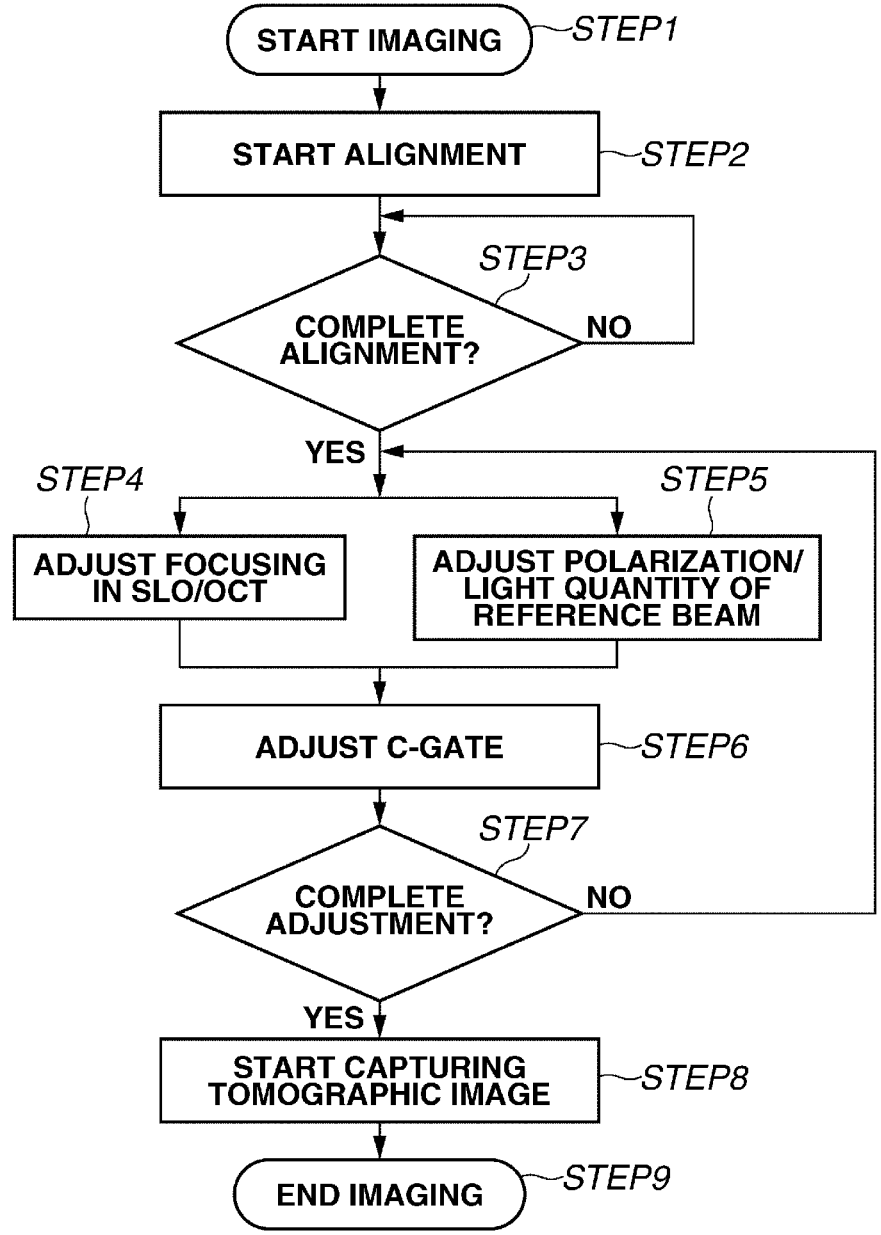
FIG. 3 is a flow chart illustrating processing performed by the respective components in the ophthalmic system according to the exemplary embodiment.

With reference to a flow chart in FIG. 3, processing which is performed when the examiner selects "Auto" of the alignment mode selection buttons 1004 on the measurement screen 1000 will be described below. In Step 1, an imaging process is started. Then, in Step 2, an alignment process (alignment between the subject's eye and the apparatus) is started.

In Step 3, if proper alignment is achieved, the examiner completes the alignment process (YES in Step 3), and then the processing proceeds to Step 4 or Step 5. If proper alignment is not achieved (NO in Step 3), the alignment process is continuously performed until proper alignment is achieved. Alternatively, the alignment process may be continuously performed without being completed, and when proper alignment is achieved, the processing may proceed to Step 4 or Step 5.

In Step 4, focus adjustment is performed in the SLO and the OCT. In Step 5, polarization of either the measuring beam or the reference beam is adjusted. In Step 5, the light quantity of the reference beam is also adjusted. Although either Step 4 or Step 5 is performed in the flow chart, Steps 4 and 5 may both be performed.

In Step 6, the coherence gate position is adjusted. In Step 7, if the adjustment of the coherence gate position is completed (YES in Step 7), the processing proceeds to Step 8. Whereas If not (NO in Step 7), the adjustment process is continuously performed until the adjustment is completed.

In Step 8, capturing of a tomographic image is started. In Step 9, the capturing is completed.

Manual adjustment is prohibited during a time period from the automatic adjustment to the image capturing. For example, the examiner cannot manually adjust the focus position (that is, cannot give an instruction to change the focus position) during the automatic adjustment of the coherence gate position (during the time period in which the optical-path-length difference changing unit exercises control). This configuration can prevent an unnecessary increase in the time required for the adjustment.

Alternatively, the foregoing processing until adjustment using a preview may be performed automatically, and then the capturing an image may be performed manually. More specifically, after the adjustment is complete in Step 7, the examiner may press the imaging button 1003 to capture a required image. In that case, after the completion of the automatic adjustment, the manual adjustment mode is automatically selected and the prohibition of manual adjustment during the automatic adjustment is removed (that is, the manual adjustment is permitted). Further, the alignment process may be continuously performed during the image capturing. Accordingly, even if involuntary eye movement during visual-fixation or the like of the subject's eye occurs during the image capturing, misalignment between the apparatus and the subject's eye can be minimized.

Aspects of the present invention can also be realized by a computer of a system or apparatus (or devices such as a CPU or an MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims the benefit of Japanese Patent Application No. 2011-079363, filed Mar. 31, 2011, which is hereby incorporated by reference herein in its entirety.

The invention claimed is:

1. A medical system comprising:
an acquisition unit configured to acquire a tomographic image of an object to be examined based on a combined beam generated by combining a return beam returning from the object to be examined illuminated with a measuring beam and a reference beam corresponding to the measuring beam;
a focus position changing unit configured to change a focus position of the measuring beam on the object to be examined;
an optical-path-length difference changing unit configured to change a difference in optical path length between the measuring beam and the reference beam;
an instruction unit configured to instruct a change of the focus position; and
a control unit configured to control the focus position changing unit not to change the focus position in a case where the instruction unit instruct the change of the focus position during a control of the optical-path-length difference changing unit and to control the focus position changing unit in accordance with the change instructed by the instruction unit in a case where the instruction unit instructs the change of the focus position after completion of the control of the optical-path-length difference changing unit.

2. The medical system according to claim 1,
wherein the control unit controls the optical-path-length difference changing unit such that the difference in optical path length is within a predetermined range,
in a case where the difference in optical path length is within the predetermined range, further comprising a display control unit configured to cause a display unit to display the tomographic image in a predetermined display position.

3. The medical system according to claim 1, wherein the control unit prohibits the focus position changing unit from changing the focus position in a case where the instruction unit instructs the change of the focus position during an automatic change of the difference in optical path length, and allows the focus position changing unit to change the focus position in a case where the instruction unit instructs the change of the focus position after completion of the automatic change of the difference in optical path length.

4. The medical system according to claim 1, further comprising a light changing unit configured to change at least one of a light quantity of the reference beam and polarization of at least one of the reference beam and the measuring beam,
wherein the control unit prohibits the light changing unit from making a manual change during an automatic change of the difference in optical path length.

5. The medical system according to claim 1, wherein after completion of an automatic change of the focus position, an automatic change of the difference in optical path length is performed.

6. The medical system according to claim 1, further comprising a selection unit configured to select an automatic change mode or a manual change mode,
wherein if the automatic change mode is selected by the selection unit, the manual change mode is automatically selected upon completion of the automatic change mode.

7. An imaging apparatus comprising:
an acquisition unit configured to acquire a tomographic image of an object to be examined based on a combined beam generated by combining a return beam returning from the object to be examined illuminated with a measuring beam and a reference beam corresponding to the measuring beam;
a focus position changing unit configured to change a focus position on the object to be examined;
an optical-path-length difference changing unit configured to change a difference in optical path length between the measuring beam and the reference beam; and
a control unit configured to control the optical-path-length difference changing unit so that the difference in the optical path length is within a predetermined range and then receive an instruction to the focus position changing unit to make a change.

* * * * *